US00PP37242P2

(12) United States Plant Patent
Hesselein

(10) Patent No.: US PP37,242 P2
(45) Date of Patent: Feb. 3, 2026

(54) ***CALYCANTHUS* PLANT NAMED 'PRNCFS'**

(50) Latin Name: ***Calycanthus floridus* var. *purpureus***
Varietal Denomination: PRNCFS

(71) Applicant: Richard Lesley Hesselein, Allentown, NJ (US)

(72) Inventor: Richard Lesley Hesselein, Allentown, NJ (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/964,922

(22) Filed: Dec. 2, 2024

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ... A01H 5/12; A01H 5/02; A01H 5/00; A01H 6/00
See application file for complete search history.

(56) References Cited

U.S. PATENT DOCUMENTS

PP28,886 P2 * 1/2018 Hesselein ..... Plt./226

* cited by examiner

*Primary Examiner* — June Hwu

(57) ABSTRACT

A new and distinct cultivar of *Calycanthus* plant named 'PRNCFS' is disclosed, characterized by dark purple foliage, with the dark purple color distinctively extending to both the upper and lower surfaces of the leaves. Leaves are large, broad and glossing, emerging purple and remain purple throughout the growing season. Flowers are red and without fragrance. Plants are compact, well-branched with a rounded/mounded habit. The new cultivar has shown greater rooting ability for production of conventional cuttings when compared to commercial varieties. The new variety is a *Calycanthus*, normally produced as an outdoor garden plant.

3 Drawing Sheets

Latin name of the genus and species: *Calycanthus floridus* var. *purpureus*.

Variety denomination: 'PRNCFS'.

BACKGROUND OF THE INVENTION

The new *Calycanthus* cultivar is a product of a naturally-occurring branch mutation. The sport originated from the parent, an unpatented, unnamed internal selection of *Calycanthus floridus* var. *purpureus*. The new variety 'PRNCFS' was discovered by the inventor in May of 2011 at a nursery in Allentown, New Jersey.

Asexual reproduction of the new cultivar 'PRNCFS' was first performed using semi-hardwood cuttings. This occurred during June of 2016, at the same nursery in Allentown, New Jersey. Subsequent propagation by softwood cuttings has shown that the unique features of this cultivar are stable and reproduced true to type in 7 successive generations.

SUMMARY OF THE INVENTION

The cultivar 'PRNCFS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PRNCFS' These characteristics in combination distinguish 'PRNCFS' as a new and distinct *Calycanthus* cultivar:

1. Dark purple foliage, with the dark purple color extending to both the upper and lower surfaces of the leaves.

2. Leaves which emerge purple and remain purple throughout the growing season.
3. Leaves which are large, broad, and glossy.
4. A compact, well-branched, rounded/mounded habit.
5. Red flowers without fragrance.
6. Greater rooting ability for conventional cuttings than comparable cultivars.

PARENT COMPARISON

Plants of the new cultivar 'PRNCFS' are similar to plants of the seed parent in most horticultural characteristics, however, plants of the new cultivar 'PRNCFS' differ in the following;

1. Foliage color of the new variety is dark purple, extending to both the upper and lower surfaces of the leaves. Foliage color of the parent is only purple on the upper surface of the leaves.

COMMERCIAL COMPARISON

Plants of the new cultivar 'PRNCFS' can be compared to the unpatented commercial variety *Calycanthus* 'Burgundy Spice', U.S. Plant Pat. No. 28,886. These varieties are similar in most horticultural characteristics; however, 'PRNCFS' differs in the following:

1. Flowers of the new variety are not fragrant, while flowers of this comparator have a sweet, fruity fragrance.

2. Plants of the new variety have a higher rooting percentage of propagules than plants of this comparator.

BRIEF DESCRIPTION OF THE PHOTOGRAPHS

The accompanying photograph in FIG. 1 illustrates in full color a typical plant of 'PRNCFS' shown in a 3-gallon container outdoors in Grand Haven, Michigan.

Figure 1:
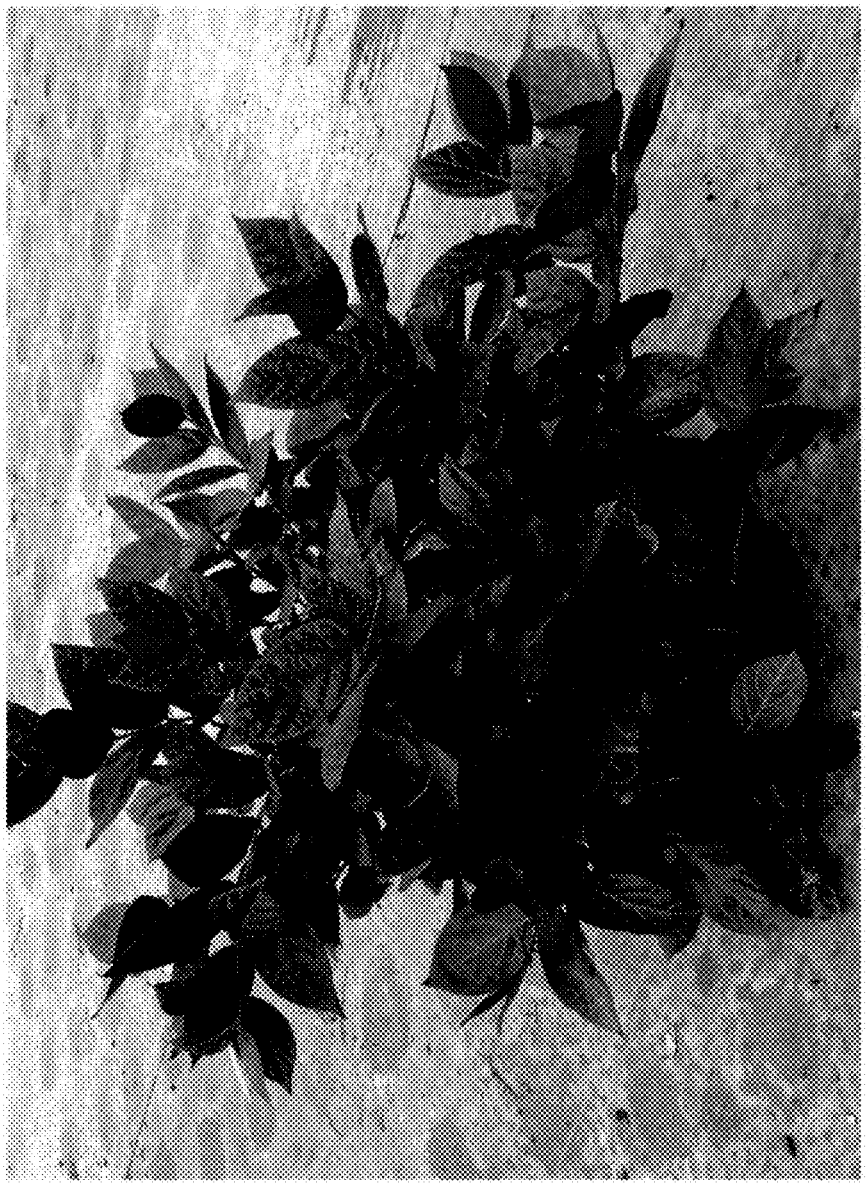
Figure 2:
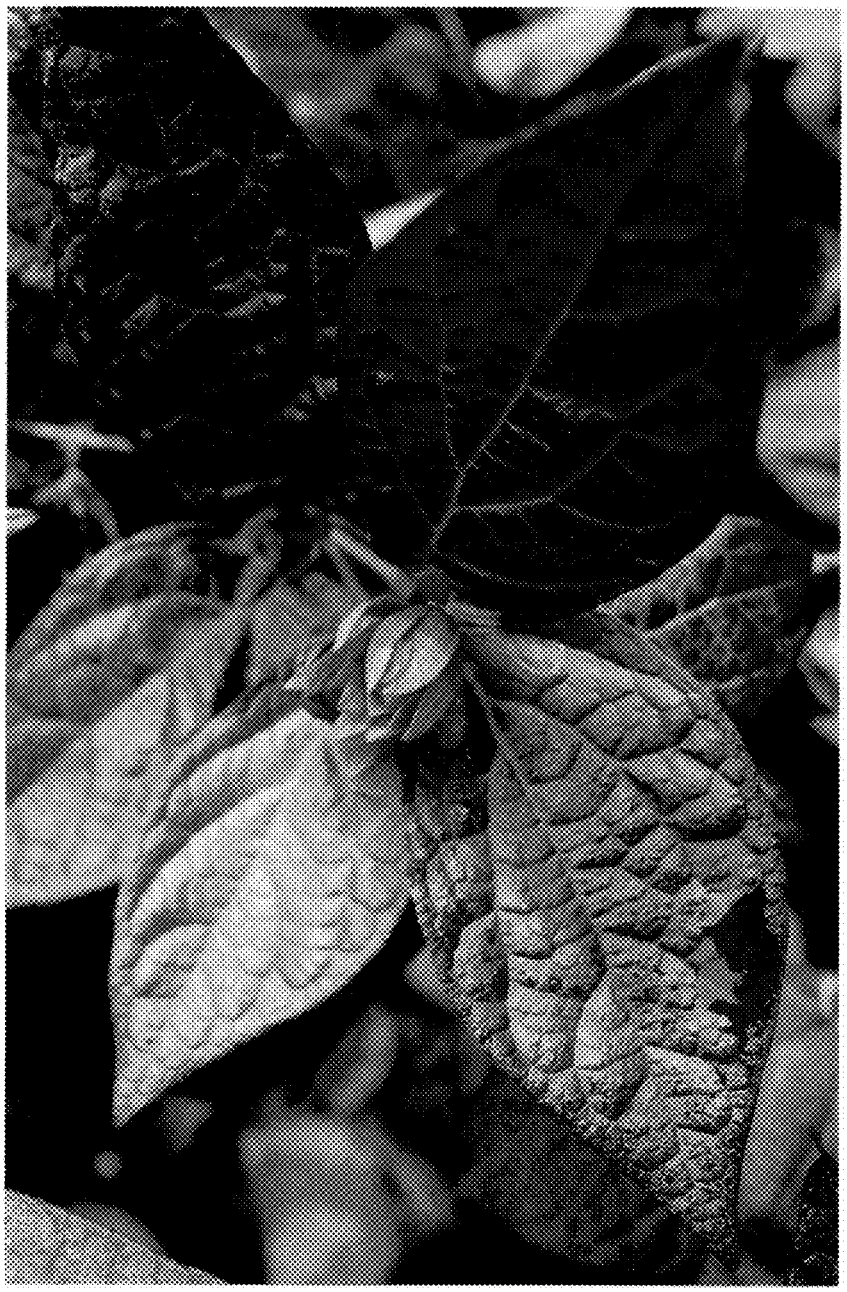
FIG. 2 illustrates in full color a close-up view of the flower.
Figure 3:
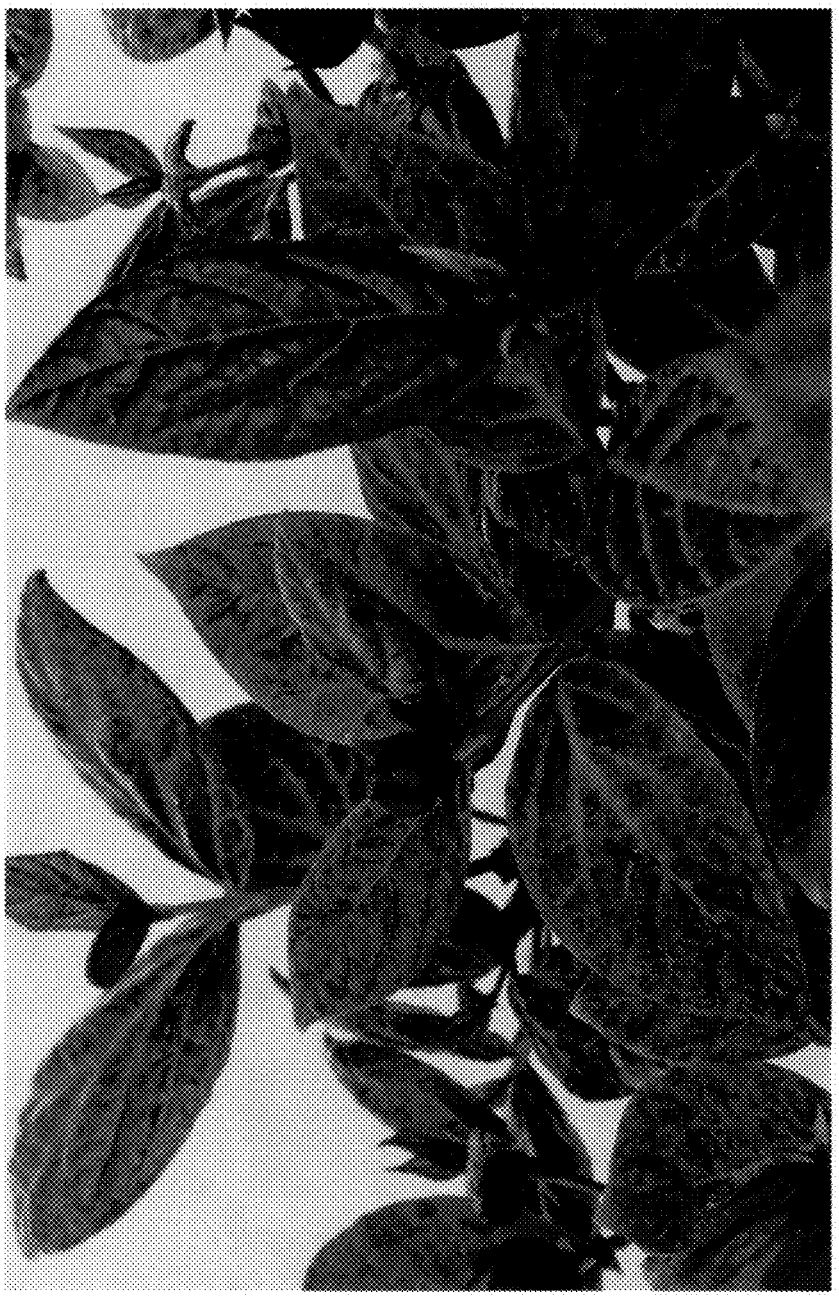
FIG. 3 illustrates a close-up of typical foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'PRNCFS' plants grown in poly-greenhouse in Grand Haven, Michigan, under natural lighting. Measurements were taken during Summer of 2018. The plants were 3 years old in #3 containers. The growing temperature ranged from 18° C. to 27° C. during the day, to 5° C. to 10° C. at night. Measurements and numerical values represent averages of typical plant types.

Botanical classification: *Calycanthus floridus purpureus* 'PRNCFS'.

PROPAGATION

Time to initiate roots: 28 days at 18° C. to 27° C.

Time to produce a rooted young plant: 48 days at 18° C. to 27° C.

Roots: Moderate density, moderate branching. Medium thickness and fleshy. Brown in color, not accurately measured with The R.H.S. Chart.

PLANT

Plant type: Perennial shrub.
Age of plant described: 3 years.
Growth habit: Upwards and outwards.
Pot size of plant described: 3-gallon.
Appropriate containers sizes: 1, 2, 3 and 5 gallon containers.
Overall plant shape: Upright, rounded/mounded.
Height: 55 cm.
Plant spread: 100 cm.
Growth rate: Moderate.
Plant vigor: Moderately vigorous.
Branching characteristics: Basal; some pinching to encourage well-branched habit.
Length of primary lateral branches: 60 to 70 cm.
Diameter of lateral branches: 6 mm.
Quantity of lateral branches: 20.
Internode length: 4 cm.
Stem:
- *Stem shape*.—Rounded.
- *Stem strength*.—Strong, rigid.
- *Angle*.—20° to 70° from center.
- *Stem color*.—New Growth: RHS Brown 200B. Old Growth: RHS Grey-Brown N199B.
- *Pubescence*.—None.

FOLIAGE

Leaf:
- *Arrangement*.—Opposite, single.
- *Leaf shape*.—Elliptic.
- *Length*.—10 cm.
- *Width* 5.5 cm.
- *Apex*.—Acute.
- *Base*.—Rounded.
- *Margin*.—Entire.
- *Texture of top surface*.—Coarse, glabrous.
- *Texture of bottom surface*.—Very lightly pubescent with short, pale hairs, especially along midrib.
- *Pubescence*.—Slight pubescence on underside.
- *Color*.—Young foliage upper side: RHS Brown 200A. Young foliage under side: Between RHS Brown 200B and Purple N77A. Mature foliage upper side: RHS Brown 200A. Mature foliage under side: Between RHS Brown 200B and Purple N77A. Fall Foliage upper side: Greyed-Purple 181A flushed Red 43A and 45A. Fall Foliage under side: Greyed-Purple 181A.
- *Venation*.—Pattern: Pinnate. New Foliage: Color upper side: RHS Yellow-Green 144B. Color under side: RHS Greyed-Purple 183A. Mature Foliage: Color upper side: RHS Greyed-Purple 187A. Color under side: RHS Greyed-Purple 183A.
- *Petiole*.—Length: 5 mm. Diameter: 2 mm. Petiole color upper side: RHS Greyed-Orange 166A. Petiole color lower side: RHS Greyed-Purple 183A. Petiole Texture upper side: Very lightly pubescent. Petiole Texture lower side: Very lightly pubescent.
- *Foliage fragrance*.—Moderate sweet and fruity when crushed.

FLOWER

Natural flowering season: May to June.
Flower arrangement: Single axial flowers along the lengths of lateral branches.
Flower form: Single rotate flowers with many strap-like tepals.
Flowering habit: Axially along the lengths of lateral branches.
Quantity of flowers per lateral stem: 3 to 5.
Quantity of flower buds per lateral stem: 3 to 5.
Quantity of flowers and buds per plant: About 100.
Individual flowers:
- *Form*.—Multi-layered strap-like tepals in a whorl, curling inward and somewhat closed.
- *Aspect*.—Upwards and outwards.
- *Diameter*.—4 cm.
- *Length*.—4 cm.
- *Depth*.—2 cm.
- *Longevity*.—2 to 3 weeks on plant.
- *Persistence*.—Self-cleaning.
- *Fragrance*.—None.

Tepals:
- *Shape*.—Strap-like, oblong.
- *Arrangement*.—Whorl, with outermost tepals laying almost flat and innermost tepals curling inwards.

*Number*.—25 to 30 per flower.
*Tepal fused*.—No.
*Tepal base*.—Blunt, flat.
*Margin*.—Entire.
*Tip shape*.—Acute.
*Length*.—2 cm.
*Width*.—5 mm.
*Texture*.—Soft and somewhat coriaceous, upper and lower surfaces.
*Color*.—When opening: Upper surface: RHS Greyed-Purple 183A. Lower surface: RHS Greyed-Purple 183A. Fully opened: Upper surface: RHS Greyed-Purple 183A. Lower surface: RHS Greyed-Purple 183A.

Bud:
*Shape*.—Ovoid.
*Length*.—1 cm.
*Diameter*.—8 mm.
*Aspect*.—Upright.
*Color*.—RHS Greyed-Purple N186C.

Peduncle:
*Length*.—1 cm.
*Diameter*.—2 mm.
*Angle*.—45° to 60°.
*Color*.—RHS Yellow-Green 144B.
*Strength*.—Good.
*Texture*.—Glabrous.

REPRODUCTIVE ORGANS

Stamens:
*Number*.—About 10.

Anthers:
*Shape*.—Oblong.
*Length*.—2 mm.
*Color*.—RHS Yellow-Green 150D.
*Pollen color*.—RHS Greyed-Yellow 160B.
*Pollen amount*.—Little.

Pistil:
*Number*.—About 15.
*Length*.—1 to 2 mm.
*Style*.—Length: 1 mm. Color: RHS Yellow-Green 145C.
*Stigma*.—Shape: Globose. Color: RHS Yellow-Green 145C. Ovary Color: RHS Yellow-Green 145C.

OTHER CHARACTERISTICS

Fruit and seed: Flowers give rise to urceolate seed capsules which enclose tens of 1-seeded achenes. Capsules about 3.5 cm long and 2 cm in diameter. Colored Greyed-Orange 166A. Seeds colored Brown 200B. About 7 mm long and 3 mm wide.

Disease/pest resistance: Neither resistance nor susceptibility to normal diseases and pests of *Calycanthus* observed.

Temperature tolerance: Tolerant to USDA Zones 4-9.

What is claimed is:

1. A new and distinct cultivar of *Calycanthus* plant named 'PRNCFS' as herein illustrated and described.

* * * * *